(12) United States Patent
Hayam et al.

(10) Patent No.: US 11,857,307 B2
(45) Date of Patent: *Jan. 2, 2024

(54) FINDING THE ORIGIN OF AN ARRYTHMIA (71) Applicants: Biosense Webster (Israel) Ltd., Yokneam (IL); Rutgers, The State University of New Jersey, New Brunswick, NJ (US)

(72) Inventors: Gal Hayam, Tivon (IL); Michael Timofeyev, Nesher (IL); Tal Haim Bar-On, Kiryat Tivon (IL); Amardeep Saluja, Brooklyn, NY (US)

(73) Assignees: BIOSENSE WEBSTER (ISRAEL) LTD., Yokneam (IL); RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/883,342

(22) Filed: Aug. 8, 2022

(65) Prior Publication Data
US 2022/0369951 A1 Nov. 24, 2022

Related U.S. Application Data

(62) Division of application No. 16/663,945, filed on Oct. 25, 2019, now Pat. No. 11,445,935.
(Continued)

(51) Int. Cl.
*A61B 5/06* (2006.01)
*A61B 34/20* (2016.01)
(Continued)

(52) U.S. Cl.
CPC ............ *A61B 5/062* (2013.01); *A61B 5/0042* (2013.01); *A61B 5/0044* (2013.01);
(Continued)

(58) Field of Classification Search
None
See application file for complete search history.

(56) References Cited

U.S. PATENT DOCUMENTS

| | | | |
|---|---|---|---|
| 5,433,198 | A | 7/1995 | Desai |
| 5,657,755 | A | 4/1997 | Desai |

(Continued)

FOREIGN PATENT DOCUMENTS

| | | | |
|---|---|---|---|
| CN | 105361945 A | 3/2016 | |
| EP | 1070480 A2 | 1/2001 | |

(Continued)

OTHER PUBLICATIONS

C.D. Cantwell et al.; "Techniques for automated local activation time annotation and conduction velocity estimation in cardiac mapping",Computers in Biology and Medicine.,vol. 65, Apr. 25, 2015 (Apr. 25, 2015), pp. 229-242.

(Continued)

*Primary Examiner* — Carl H Layno
*Assistant Examiner* — Manolis Pahakis
(74) *Attorney, Agent, or Firm* — Notaro, Michalos & Zaccaria P.C.

(57) ABSTRACT

A probe generates location signals, and has an electrode at a distal end that acquires from heart chamber surface positions electrical signals due to a conduction wave traversing the surface. A processor derives LATs from the electrical signals, calculates a first time difference between LATs at a first pair of positions and a second time difference between LATs at a second pair of positions. The processor calculates first and second LAT-derived distances as products of the first and second time differences with a conduction wave velocity, identifies an arrhythmia origin at a surface location where a first difference in distances from the location to the first pair of the positions is equal to the first LAT-derived (Continued)

distance, and a second difference in distances from the location to the second pair of the positions is equal to the second LAT-derived distance, and marks the origin on a surface representation.

5 Claims, 9 Drawing Sheets

Related U.S. Application Data (60) Provisional application No. 62/771,360, filed on Nov. 26, 2018.

(51) Int. Cl.
    *A61B 5/0538*      (2021.01)
    *G06T 17/20*      (2006.01)
    *A61B 5/283*      (2021.01)
    *A61B 5/364*      (2021.01)
    *A61B 5/287*      (2021.01)
    *A61B 5/00*      (2006.01)
    *A61B 18/12*      (2006.01)
    *A61B 18/00*      (2006.01)
    *A61B 18/14*      (2006.01)

(52) U.S. Cl.
    CPC ............ *A61B 5/0538* (2013.01); *A61B 5/283* (2021.01); *A61B 5/287* (2021.01); *A61B 5/364* (2021.01); *A61B 5/4836* (2013.01); *A61B 5/7235* (2013.01); *A61B 5/743* (2013.01); *A61B 18/12* (2013.01); *A61B 34/20* (2016.02); *G06T 17/20* (2013.01); *A61B 5/6847* (2013.01); *A61B 2018/00351* (2013.01); *A61B 2018/00577* (2013.01); *A61B 2018/00595* (2013.01); *A61B 2018/1467* (2013.01); *A61B 2034/2046* (2016.02); *A61B 2576/023* (2013.01); *G06T 2210/41* (2013.01)

(56) References Cited

U.S. PATENT DOCUMENTS

| | | | |
|---|---|---|---|
| 6,301,496 B1 * | 10/2001 | Reisfeld | G06T 17/20 600/407 |
| 6,690,963 B2 | 2/2004 | Ben-Haim et al. | |
| 8,456,182 B2 | 6/2013 | Bar-Tal et al. | |
| 8,577,450 B1 | 11/2013 | Chmiel et al. | |
| 9,101,333 B2 | 8/2015 | Schwartz | |
| 9,649,046 B2 | 5/2017 | Bar-Tal et al. | |
| 10,136,828 B2 | 11/2018 | Houben et al. | |
| 10,314,542 B2 | 6/2019 | Bar-Tal et al. | |
| 10,403,053 B2 | 9/2019 | Katz et al. | |
| 10,576,263 B2 | 3/2020 | Botzer et al. | |
| 10,786,166 B2 | 9/2020 | Cohen et al. | |
| 10,842,400 B2 | 11/2020 | Bar-Tal et al. | |
| 10,856,759 B2 | 12/2020 | Bar-Tal et al. | |
| 11,109,788 B2 * | 9/2021 | Rottmann | A61B 5/287 |
| 2002/0010392 A1 | 1/2002 | Desai | |
| 2002/0005567 A1 | 3/2002 | Shlomo et al. | |
| 2003/0176778 A1 | 9/2003 | Messing et al. | |
| 2004/0059237 A1 | 3/2004 | Narayan et al. | |
| 2005/0203375 A1 | 9/2005 | Willis et al. | |
| 2006/0161206 A1 * | 7/2006 | Efimov | A61N 1/3627 607/14 |
| 2010/0094597 A1 * | 4/2010 | Blain | G06T 17/20 703/1 |
| 2011/0144510 A1 | 6/2011 | Ryu et al. | |
| 2013/0006131 A1 | 1/2013 | Narayan et al. | |
| 2013/0274582 A1 | 10/2013 | Afonso et al. | |
| 2013/0324871 A1 * | 12/2013 | Dubois | A61B 5/7271 600/509 |
| 2014/0088447 A1 * | 3/2014 | Massarwa | A61B 5/0538 600/508 |
| 2014/0176531 A1 * | 6/2014 | Rubinstein | G06T 19/00 345/419 |
| 2014/0330111 A1 * | 11/2014 | Lichtenstein | G06T 15/10 600/508 |
| 2015/0073246 A1 | 3/2015 | Chmiel et al. | |
| 2016/0038047 A1 * | 2/2016 | Urman | A61B 5/7485 600/509 |
| 2016/0045123 A1 * | 2/2016 | Bar-Tal | A61B 5/287 600/515 |
| 2016/0155274 A1 * | 6/2016 | Merschon | A61B 5/339 345/419 |
| 2017/0049348 A1 | 2/2017 | Deno et al. | |
| 2017/0172508 A1 | 6/2017 | Hultz et al. | |
| 2017/0202470 A1 | 7/2017 | Urman et al. | |
| 2017/0202472 A1 | 7/2017 | Zeidan et al. | |
| 2017/0202515 A1 | 7/2017 | Zrihem et al. | |
| 2017/0202521 A1 | 7/2017 | Urman et al. | |
| 2017/0221254 A1 * | 8/2017 | Zar | G06T 17/00 |
| 2017/0232263 A1 | 8/2017 | Narayan et al. | |
| 2017/0281031 A1 * | 10/2017 | Houben | A61B 18/1492 |
| 2018/0137687 A1 * | 5/2018 | Katz | A61B 18/1492 |
| 2018/0158238 A1 * | 6/2018 | Cohen | G06T 19/20 |
| 2018/0189969 A1 * | 7/2018 | Bustan | G06T 19/20 |
| 2018/0190009 A1 * | 7/2018 | Cohen | G06F 3/04812 |
| 2018/0235692 A1 | 8/2018 | Efimov et al. | |
| 2018/0256056 A1 * | 9/2018 | Lu | A61B 5/319 |
| 2019/0259490 A1 * | 8/2019 | Cohen | A61B 5/339 |
| 2019/0261876 A1 * | 8/2019 | Ghosh | A61B 5/1107 |
| 2019/0279773 A1 * | 9/2019 | Shamilov | A61B 5/319 |
| 2019/0298213 A1 | 10/2019 | Niederer et al. | |
| 2019/0328254 A1 | 10/2019 | Villongco | |
| 2019/0328258 A1 * | 10/2019 | Gaeta | A61B 5/061 |
| 2020/0060567 A1 | 2/2020 | Zeida et al. | |
| 2020/0146572 A1 * | 5/2020 | Bar-Tal | A61B 5/341 |
| 2020/0146579 A1 * | 5/2020 | Bar-Tal | A61B 5/287 |
| 2020/0163582 A1 | 5/2020 | Hayam et al. | |
| 2020/0359924 A1 | 11/2020 | Finlay et al. | |
| 2020/0367751 A1 | 11/2020 | Vandersickel et al. | |
| 2020/0405393 A1 | 12/2020 | Villongco | |
| 2021/0065906 A1 | 3/2021 | Villongco | |
| 2021/0259610 A1 | 8/2021 | Villongco | |
| 2022/0000410 A1 | 1/2022 | Baram et al. | |
| 2022/0079499 A1 | 3/2022 | Doron et al. | |

FOREIGN PATENT DOCUMENTS

| | | |
|---|---|---|
| EP | 2982293 A1 | 2/2016 |
| WO | 2017184679 A1 | 10/2017 |
| WO | 2018190781 A1 | 10/2018 |

OTHER PUBLICATIONS

Extended European search report for corresponding European patent application No. EP 19211138.3, dated Jan. 23, 2020.

Saluja D., Kassotis J., Kostis W.J., Coromilas J., A novel method for the prediction of focal wavefront origins in cardiac arrhythmias, Computers in Biology and Medicine 102 421-425, Epub Aug. 20, 2018. (Year: 2018), https://pubmed.ncbi.nlm.nih.gov/30274661/ , retrieved Aug. 8, 2022.

Chinese office action for corresponding Chinese application No. 201911173659. 6, dated Sep. 15, 2022.

* cited by examiner

FINDING THE ORIGIN OF AN ARRYTHMIA

CROSS-REFERENCE TO RELATED APPLICATIONS

This application is a divisional application of U.S. patent application Ser. No. 16/663,945, filed Oct. 25, 2019, which issued as U.S. Pat. No. 11,445,935 on Sep. 20, 2022 and which claims the benefits of U.S. Provisional Patent Application 62/771,360 filed Nov. 26, 2018, which are each incorporated herein by reference.

FIELD OF THE INVENTION

The present invention relates generally to invasive medical procedures, and specifically to analyzing results of a cardiac invasive procedure.

BACKGROUND OF THE INVENTION

One type of cardiac arrythmia is a single-source arrythmia where the arrythmia has a localized origin. In order to cure the arrythmia, it is important to find the localized origin. Typically, once the origin has been located, ablation may be applied to the origin, or to a region in proximity to the origin, to cure the arrythmia.

SUMMARY OF THE INVENTION

An embodiment of the present invention provides medical apparatus, consisting of:
  a probe, configured to be inserted into a chamber of a heart of a human subject, and to generate location signals indicative of location coordinates of a distal end of the probe, and including an electrode at the distal end, which is configured to acquire from positions on a surface of the chamber respective electrical signals in response to a conduction wave traversing the surface;
  a display; and
  a processor, configured to:
  process the location signals to generate and present on the display a three-dimensional (3D) representation of the surface,
  derive respective local activation times (LATs) from the respective electrical signals at the positions on the surface,
  calculate a first time difference between the respective LATs at a first pair of the positions on the surface and a second time difference between the respective LATs at a second pair of the positions on the surface,
  calculate first and second LAT-derived distances as respective products of the first time difference and the second time difference with a conduction velocity of the conduction wave,
  identify an origin of an arrhythmia at a location on the surface such that a first difference in distances over the surface from the location to the first pair of the positions is equal to the first LAT-derived distance, and a second difference in distances over the surface from the location to the second pair of the positions is equal to the second LAT-derived distance, and
  mark the identified origin on the representation of the surface on the display.

In a disclosed embodiment the first pair of the positions and the second pair of the positions consist of one common position.

In a further disclosed embodiment the processor is configured to generate a mesh from the location coordinates, and the distances over the surface include shortest distances measured along edges of the mesh. The mesh may be a triangular mesh.

In a yet further disclosed embodiment the processor may be configured to mark on the representation a first locus of first locations wherein the first difference in distances over the surface from the first locations to the first pair of the positions is equal to the first LAT-derived distance, and a second locus of second locations wherein the second difference in distances over the surface from the second locations to the second pair of the positions is equal to the second LAT-derived distance. The identified origin is typically at an intersection of the first locus and the second locus.

In an alternative embodiment the arrythmia includes a single source arrythmia.

In a further alternative embodiment the processor is configured to calculate the conduction velocity in response to a selected pair of points on the surface, the points being connected by a line segment parallel to a wavefront vector, and having respective LATs and positions.

In a yet further alternative embodiment the first difference in distances is equal to the first LAT-derived distance within a preset margin of error, and the second difference in distances is equal to the second LAT-derived distance within the preset margin of error. In one embodiment the preset margin of error is 1 mm.

An operator of the apparatus may select the first pair of positions and the second pair of positions.

There is further provided, according to an embodiment of the present invention, a method, including:
  inserting a probe into a chamber of a heart of a human subject;
  generating location signals indicative of location coordinates of a distal end of the probe;
  acquiring from positions on a surface of the chamber respective electrical signals in response to a conduction wave traversing the surface;
  processing the location signals to generate and present on a display a three-dimensional (3D) representation of the surface,
  deriving respective local activation times (LATs) from the respective electrical signals at the positions on the surface;
  calculating a first time difference between the respective LATs at a first pair of the positions on the surface and a second time difference between the respective LATs at a second pair of the positions on the surface,
  calculating first and second LAT-derived distances as respective products of the first time difference and the second time difference with a conduction velocity of the conduction wave;
  identifying an origin of an arrhythmia at a location on the surface such that a first difference in distances over the surface from the location to the first pair of the positions is equal to the first LAT-derived distance, and a second difference in distances over the surface from the location to the second pair of the positions is equal to the second LAT-derived distance; and
  marking the identified origin on the representation of the surface on the display.

The present disclosure will be more fully understood from the following detailed description of the embodiments thereof, taken together with the drawings, in which:

DETAILED DESCRIPTION OF EMBODIMENTS

Overview

Embodiments of the present invention initially generate a map of a heart chamber where a single-source arrythmia is present, and in addition measure local activation times (LATs) over the surface of the chamber. The arrythmia is assumed to radiate a conduction wave from an origin, so that at a given point on the surface of the chamber the LAT for that point is indicative of the time at which the wave from the origin passes the point.

If a pair of points on the surface is selected, the points will typically have different LATs, and the difference in the LATs gives a measure of the difference in distance from the two points to the arrythmia origin. The actual difference in distance is the product of the conduction wave velocity and the LAT difference, and this is termed herein an LAT-derived distance. (It will be understood that if the two points have the same LATs, they are equidistant from the arrythmia origin.)

From the selected pair of points, a locus of possible positions for the arrythmia origin can be found, all the points on the locus having the actual difference in distance to the selected pair that is described above.

If another pair of points on the surface is selected the same procedure, to find a second locus of positions for the arrythmia origin, can be applied to the second pair of points.

The intersection of the loci corresponds to the position of the origin of the arrythmia, and this may be displayed on the map. The loci themselves may also be displayed on the map.

It will be understood that the origin location is such that a difference in distances over the surface from the origin location to a first pair of the points is equal to the LAT-derived distance for the first pair, and is also such that a difference in distances over the surface from the origin location to a second pair of the points is equal to the second LAT-derived distance for the second pair.

Typically, the two pairs of points comprise four physically separated distinct points (in two pairs). However, in some embodiments one of the points is common to both pairs, so that in these embodiments three physically separated distinct points comprise the two pairs.

System Description

In the following description, like elements in the drawings are identified by like numerals, and like elements are differentiated as necessary by appending a letter to the identifying numeral.

Figure 1:
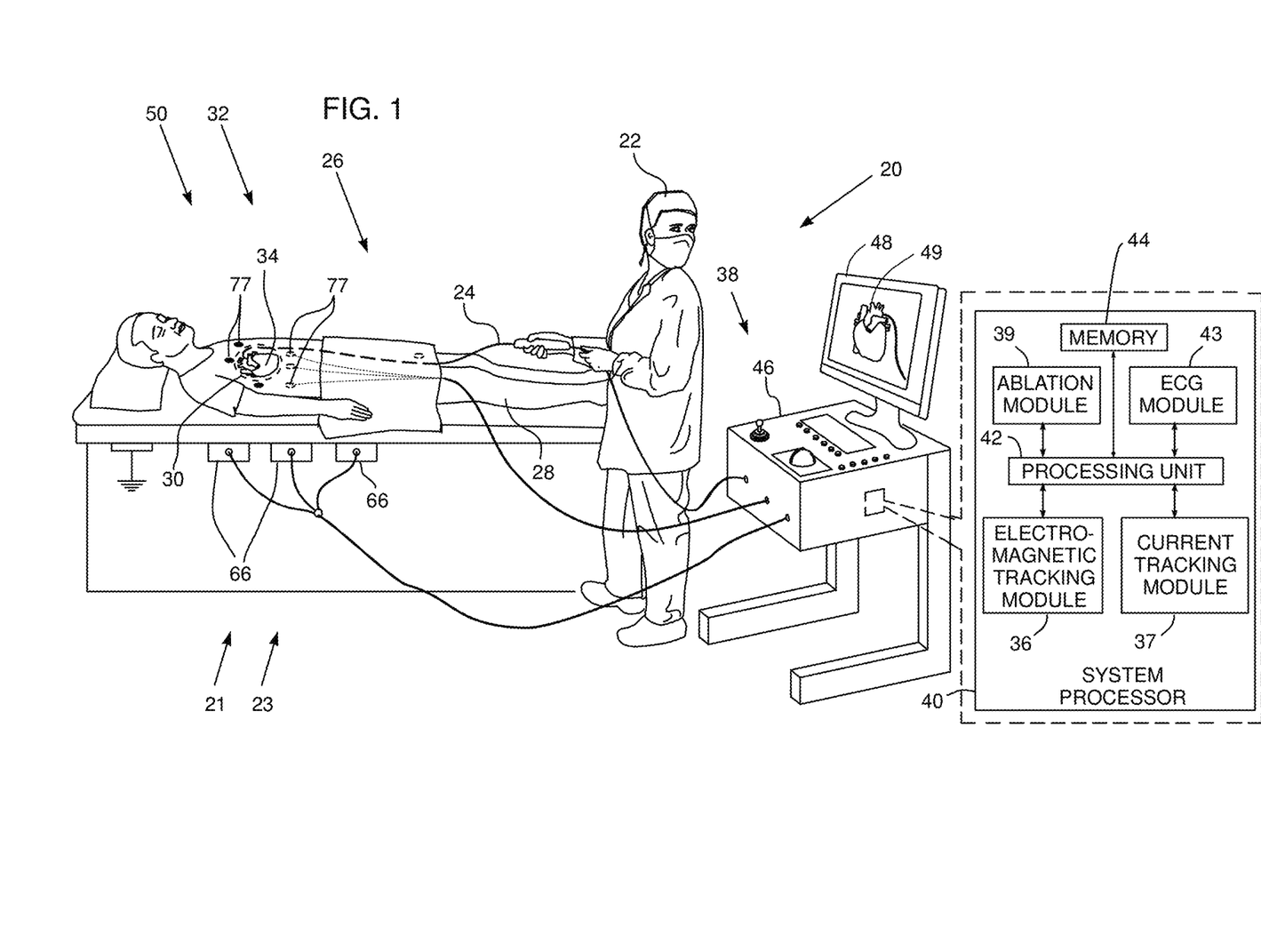
FIG. 1 is a schematic illustration of an arrythmia origin locating system, according to an embodiment of the present invention.

Reference is now made to FIG. 1, which is a schematic illustration of an arrythmia origin locating system 20, according to an embodiment of the present invention. For simplicity and clarity, the following description, except where otherwise stated, assumes a medical procedure is performed by an operator 22 of system 20, herein assumed to be a medical practitioner, wherein the operator inserts a catheter 24 into a left or right femoral vein of a patient 28. The procedure is assumed to comprise investigation of a chamber of a heart 34 of the patient, and in the procedure, the catheter is initially inserted into the patient until a distal end 32 of the catheter, also herein termed probe 32, reaches the heart chamber.

System 20 may be controlled by a system processor 40, comprising a processing unit (PU) 42 communicating with an electromagnetic tracking module 36 and/or a current tracking module 37. PU 42 also communicates with an ablation module 39 and an ECG (electrocardiograph) module 43. The functions of the modules are described in more detail below. PU 42 also communicates with a memory 44. Processor 40 is typically mounted in a console 46, which comprises operating controls 38, typically including a pointing device such as a mouse or trackball, that operator 22 uses to interact with the processor. The processor uses software stored in memory 44 to operate system 20. Results of the operations performed by processor 40 are presented to the operator on a display 48, which typically presents a map of heart 34. The software may be downloaded to processor 40 in electronic form, over a network, for example, or it may, alternatively or additionally, be provided and/or stored on non-transitory tangible media, such as magnetic, optical, or electronic memory.

For tracking the path of probe 32 in a mapping region 30 containing heart 34, embodiments of the present invention use at least one of a current based tracking system 21 and an electromagnetic based tracking system 23. Both systems are described below.

Tracking system 21 comprises a current measuring tracking system, similar to that described in U.S. Pat. No. 8,456,182 to Bar-Tal et al., whose disclosure is incorporated herein by reference. The Carto™ system produced by Biosense-Webster of 33 Technology Drive, Irvine, CA 92618 USA, also uses a current measuring tracking system. The current measuring tracking system is under control of current tracking module 37. Probe 32 has one or more probe electrodes 50, and in tracking system 21 module 37 injects currents to the one or more electrodes 50 being tracked. The currents are received, by a plurality of generally similar patch electrodes 77, also herein termed patches, which are positioned on the skin of patient 28, and transferred back to the module.

While conductive cabling to patch electrodes 77 and for other skin electrodes described herein is present for each of the electrodes, for clarity cabling is only shown in the figure for some of the electrodes. The currents between a given probe electrode 50 and skin patches 77 vary according to the location of the electrode, because, inter alia, of the different distances of the electrode from the patches, which cause different impedances between the given probe electrode and the different patches. Module 37 measures the different currents received by the different patches 77 on respective channels connected to the patches, and may be configured to generate an indication of the location of the given probe electrode from the different currents.

Electromagnetic tracking system 23 is similar to that described in U.S. Pat. No. 6,690,963 to Ben-Haim et al., whose disclosure is incorporated herein by reference, and to that used in the Carto™ system produced by Biosense-Webster. The electromagnetic tracking system is under control of electromagnetic tracking module 36. The electromagnetic tracking system comprises a plurality of magnetic field generators, herein assumed to comprise three sets of generators 66, each set comprising three orthogonal coils, so that the plurality of generators comprises a total of nine coils. Generators 66 are placed in known locations beneath patient 28, the known locations defining a frame of reference of the generators. Module 36 controls, inter alia, the amplitude and frequency of the alternating magnetic fields produced by the generators.

The alternating magnetic fields interact with a coil located in probe 32, so as to generate alternating electropotentials in the coil, and the electropotentials are received as a signal by tracking module 36. The module, together with processing unit 42, analyzes the received signal, and from the analysis is able to determine a position, i.e., a location and an orientation, of the probe coil in the defined frame of reference.

Typically the tracking by either or both of the systems may be presented visually on display 48, for example by incorporating an icon representing the probe into an image of heart 34, as well as a path taken by the icon. For clarity, in the following description, only electromagnetic tracking system 23 is assumed to be use, but the description may be adapted, mutatis mutandis, for cases where both system 23 and system 21 are used, or if only system 21 is used.

Ablation module 39 comprises a radiofrequency (RF) generator which delivers RF power to a region of heart 34 that is selected by operator 22, so as to ablate the region. Operator 22 selects the region by positioning an ablation probe, with an ablation electrode, at the region. In some embodiments probe 32 and one of electrodes 50 may be used as an ablation probe and an ablation electrode. Alternatively a separate ablation probe and ablation electrode may be used for the ablation provided by module 39.

ECG module 43 receives ECG signals from electrodes 50, and together with PU 42 analyzes the signals to find, inter alia, local activation times (LATs) of the signals. The module typically measures the LAT values relative to a reference ECG signal, such as may be provided by an electrode positioned in the coronary sinus of heart 34.

Figure 2:
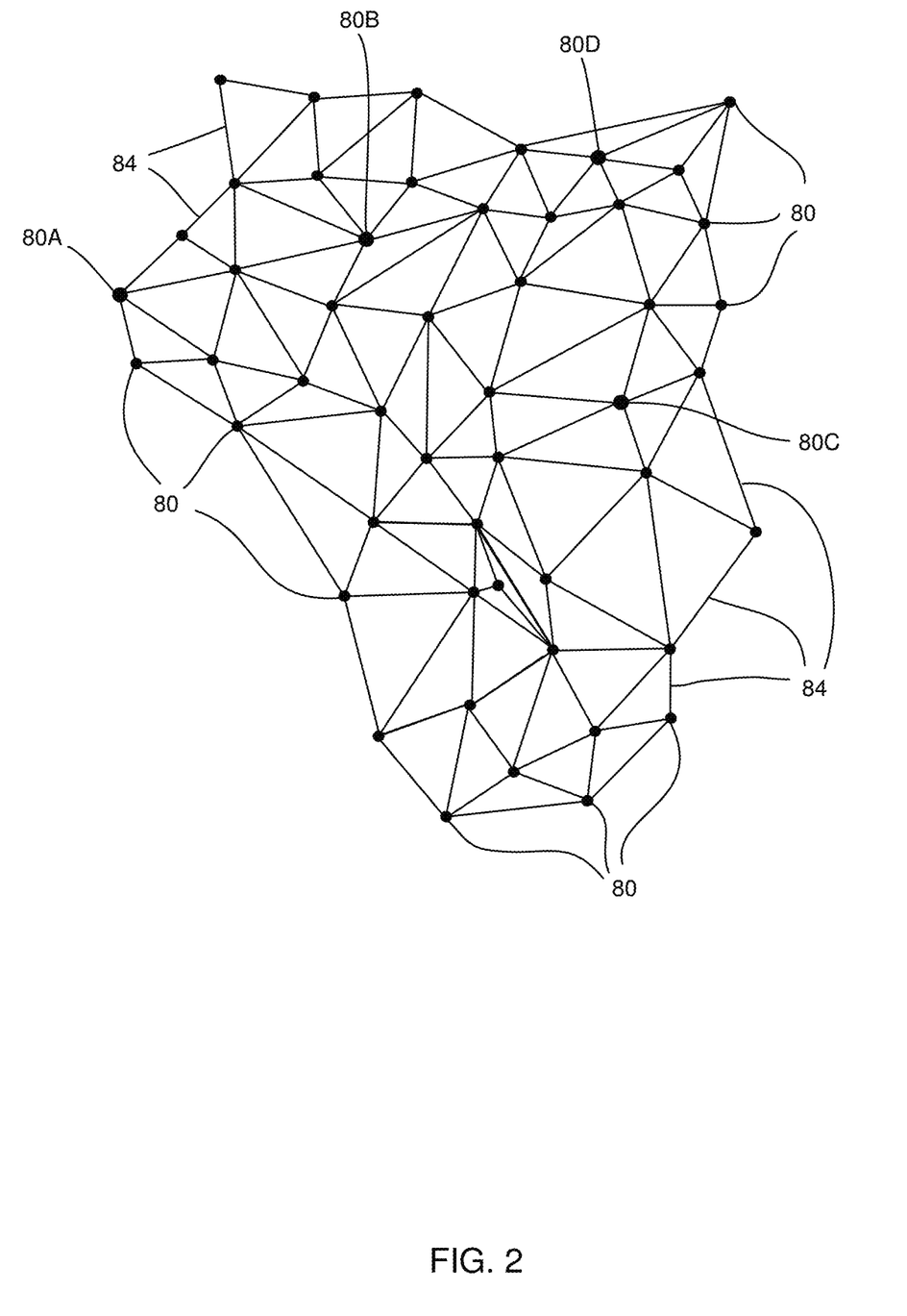
FIG. 2 is a schematic diagram illustrating results produced by an electromagnetic tracking system, according to an embodiment of the present invention.

FIG. 2 is a schematic diagram illustrating results produced by electromagnetic tracking system 23, according to an embodiment of the present invention. During the procedure referred to above, probe 32 is moved within heart 34, herein assumed to be within a chamber of the heart, and as it is moved tracking module 36 acquires positional signals from the probe, and uses the signals to find three-dimensional (3D) positions of the probe. The multiple positions found comprise a point cloud of locations on the surface of the chamber, as well as locations within the chamber.

From the point cloud processor 40 generates a triangular mesh of a 3D enclosing surface, i.e., a surface enclosing all the acquired points in the point cloud, corresponding to the surface of the heart chamber. The processor uses any method known in the art to produce the mesh. Typically processor 40 "covers" the triangular mesh to form a smooth continuous 3D surface, and the processor may display a graphic representation 49 of the smooth 3D surface on display 48. In addition, the processor typically covers triangles of the mesh with equally spaced sample points, and these points provide processor 40 with a method to perform discrete calculations on the continuous 3D surface. An example of the use of the sample points described herein is provided below, with reference to FIG. 6.

FIG. 2 schematically shows a set of points 80, comprising some of the points in the point cloud referred to above, each of the points corresponding to respective points on the surface of the heart chamber. The figure also illustrates edges 84 connecting the points, the edges corresponding to line segments joining the points when processor 40 generates the triangular mesh. Points 80 and edges 84 are vertices and sides of triangles, and are herein also termed vertices 80 and sides 84.

Figure 3:
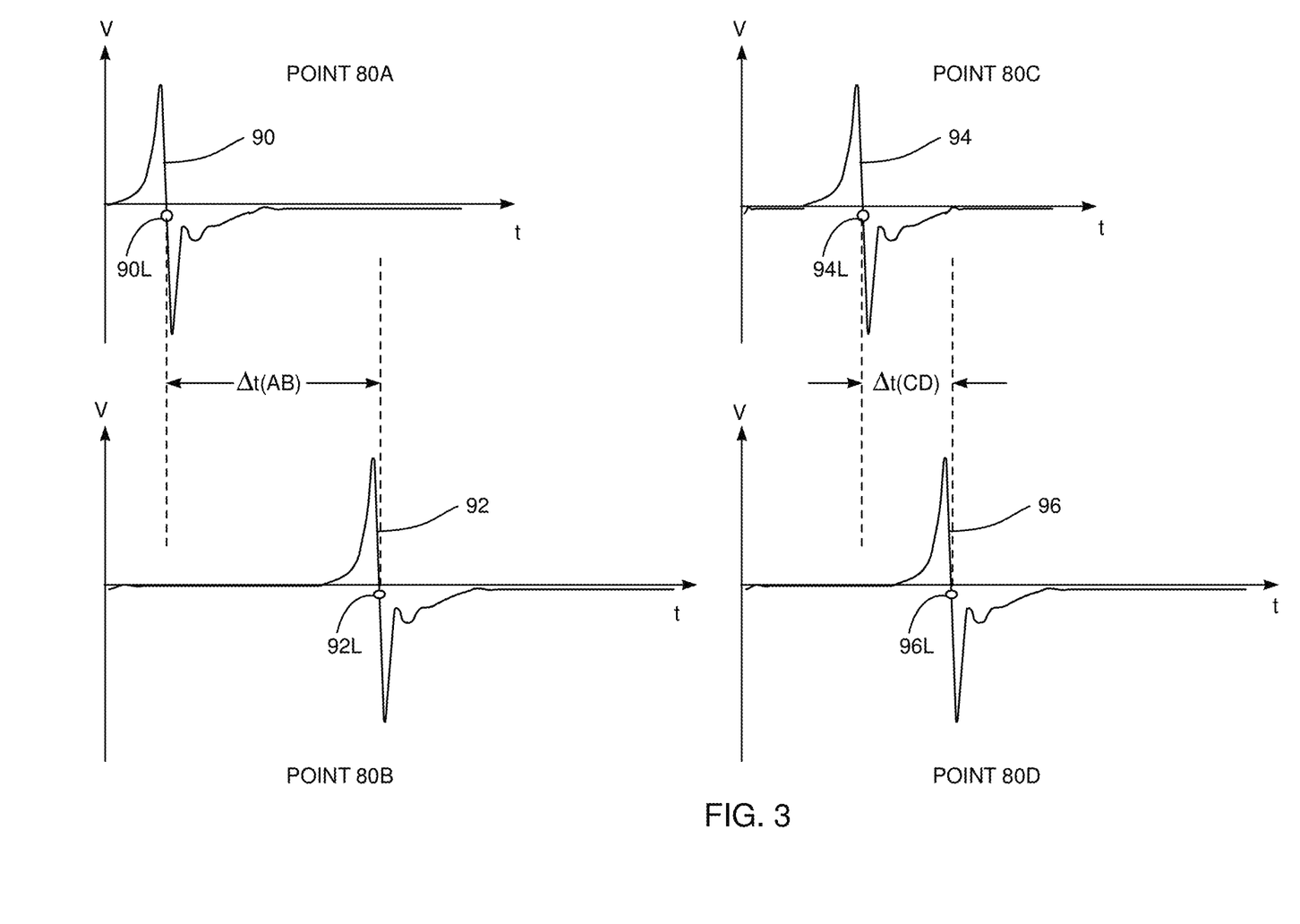
FIG. 3 is a schematic diagram of results generated by an electrocardiogram module, according to an embodiment of the present invention.

FIG. 3 is a schematic diagram of results generated by ECG module 43, according to an embodiment of the present invention. The results are generated from ECG signals acquired by probe 32 as the probe contacts the surface of the heart chamber wherein the probe is moved. The ECG signals may be acquired concurrently with the positional signals referred to above, or alternatively at a different time, and possibly with a different probe.

The figure illustrates four voltage V vs. time t graphs 90, 92, 94, 96, respectively corresponding to ECG signals acquired at four points 80A, 80B, 80C, 80D (FIG. 2) on the surface of the heart chamber. For each set of graphs the ECG module calculates the position (in time) of the local activation time (LAT), and the LAT value is shown schematically on each of the graphs as circles 90L, 92L, 94L, 96L. Each of the four graphs has been drawn with the V axis corresponding to a reference time of zero derived from the reference ECG signal referred to above.

In embodiments of the present invention processor 40 selects pairs of points 80 and calculates the difference in LAT values of the ECG signals of the points. Thus, in FIG. 3 processor 40 may select points 80A and 80B, in which case it finds the difference in LAT values as $\Delta t(AB)$. Similarly the processor may select points 80C and 80D, in which case it finds the difference in LAT values as $\Delta t(CD)$.

The following description assumes that for a general pair of points 80 selected by processor 40 the difference in LAT values of the ECG signals is $\Delta t$. Embodiments of the present invention assume that the ECG signals are generated from a single-source arrythmia, and that the ECG signals traverse the surface of the heart chamber with a conduction velocity v. In this case, for the general pair of points assumed herein there is a difference in path length $\Delta P$, from the single source to the two points of the general pair, given by equation (1):

$$\Delta P = v \cdot \Delta t \quad (1)$$

The difference in path length $\Delta P$ is a distance, and is also herein termed the LAT-derived distance.

Figure 4:
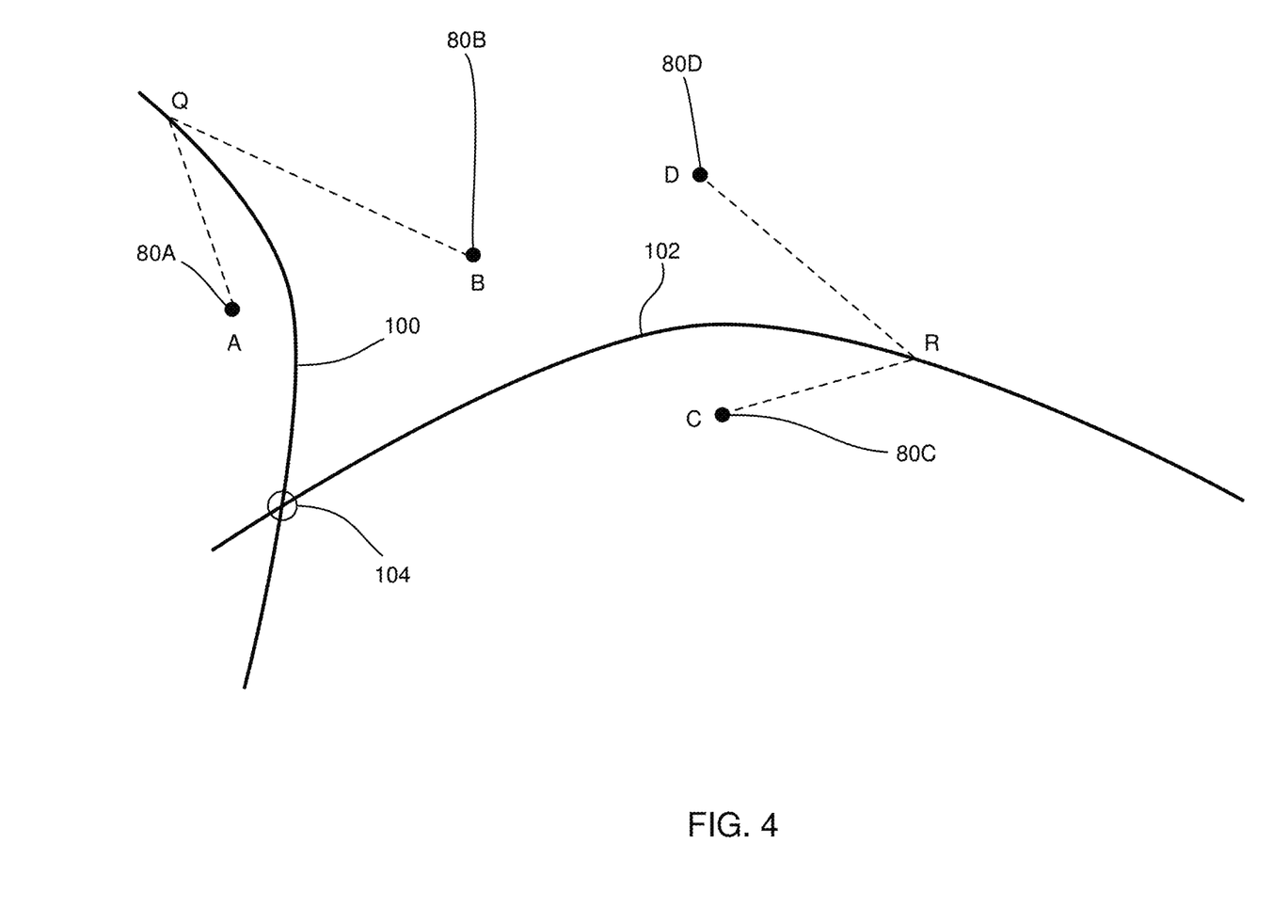
FIG. 4 illustrates how a difference in path lengths given by an equation is used for pairs of points selected by a processor, according to an embodiment of the present invention.

FIG. 4 illustrates how the difference in path lengths given by equation (1) is used for specific pairs of points 80 selected by processor 40, according to an embodiment of the present invention. The points illustrated in FIG. 4 correspond to points 80A, 80B, 80C, and 80D, (FIG. 2) and are herein respectively termed A, B, C, D.

For points A, B, a point Q can be the origin of the single source arrythmia if equation (2) is valid.

$$BQ - AQ = v \cdot \Delta t(AB) \quad (2)$$

where BQ is the distance on the surface of the heart chamber between points B and Q, AQ is the distance on the surface of the heart chamber between points A and Q, and $\Delta t(AB)$ is the difference in LAT values between the ECG signals from points B and A.

The LAT-derived distance for points A, B is the product $v \Delta t(AB)$.

It will be understood that to satisfy equation (2) the point Q may be in a plurality of locations i.e., Q may be on a locus, or line, 100, where any point on the locus obeys equation (2). Line 100 is a curved line that predicts where an origin of the single source arrythmia may be, and lines such as line 100 are also referred to herein as prediction lines.

For points C, D, a point R can be the origin of the single source arrythmia if equation (3) is valid.

$$DR - CR = v \cdot \Delta t(CD) \qquad (3)$$

where DR is the distance on the surface of the heart chamber between points D and R, CR is the distance on the surface of the heart chamber between points C and R, and $\Delta t(CD)$ is the difference in LAT values between the ECG signals between points D and C.

The LAT-derived distance for points C, D is the product $v \Delta t(CD)$.

As for equation (2), equation (3) generates a locus or line 102, and point R may be any point on the locus. Line 102 is also a prediction line for the position of the origin of the single-source arrythmia.

Loci 100 and 102 intersect at a region 104, and since region 104 is on both loci, region 104 corresponds to a predicted origin of the single-source arrythmia generating the ECG signals acquired at points 80A, 80B, 80C, and 80D.

Figure 5:
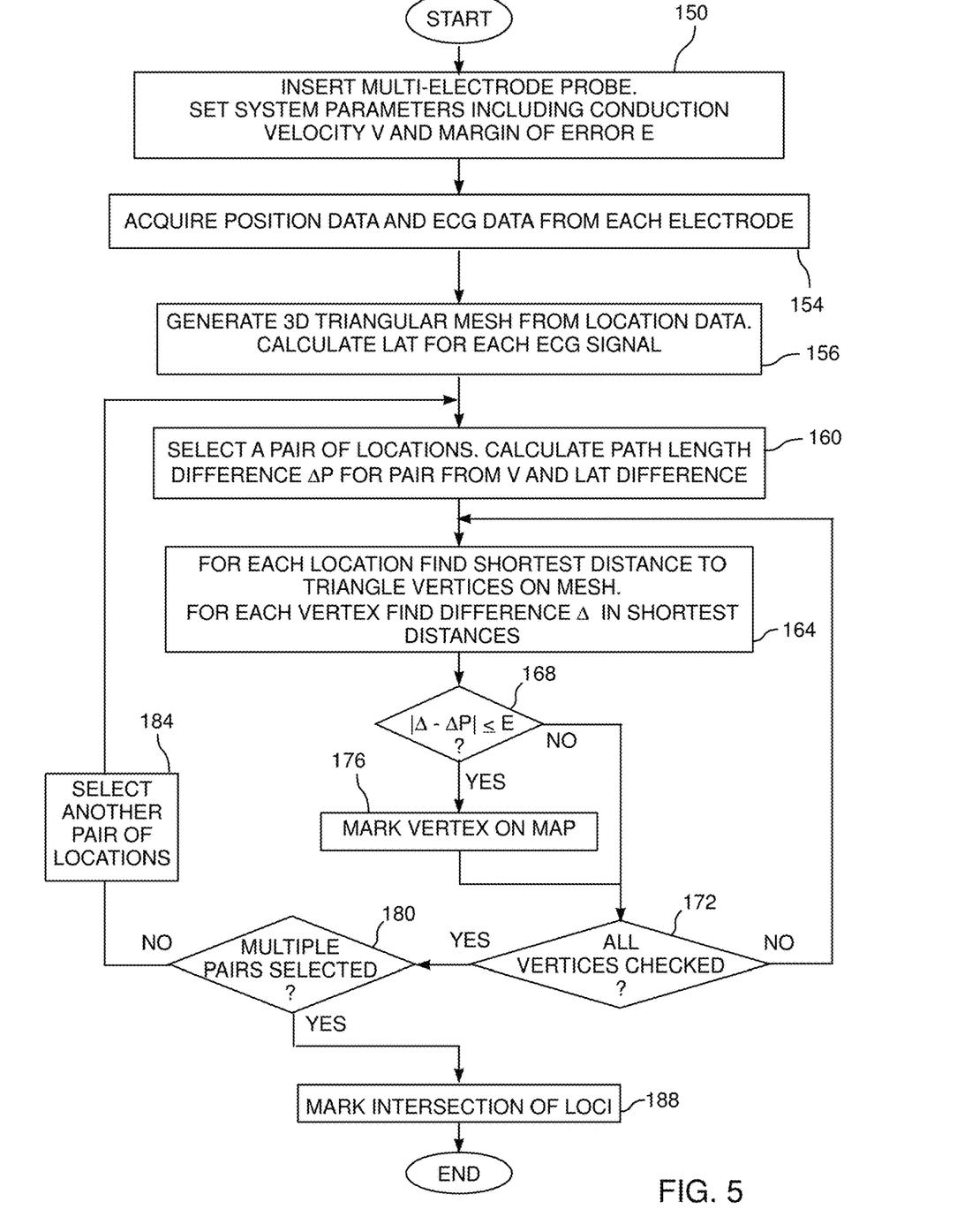
FIG. 5 is a flowchart of steps performed by a processor and an operator in determining a location of an origin of a single-source arrythmia using the system of FIG. 1, according to an embodiment of the present invention.

FIG. 5 is a flowchart of steps performed by processor 40 and operator 22 in determining the location of an origin of a single-source arrythmia using system 20, according to an embodiment of the present invention.

In an initial step 150 operator 22 inserts probe 32 into a chamber of heart 34 of the patient. Probe 32 is typically a multi-electrode probe having electrodes 50, such as the Pentaray probe produced by Biosense-Webster. The operator may also set values of parameters, such as an assumed conduction velocity in heart 34 and a margin of error to be used in evaluating results, to be used by the processor in performing its calculations for the origin location.

In one embodiment the conduction velocity v in the heart chamber is set to be 1.0 mm/ms, and an acceptable error E in determining the origin location is set to be 1 mm. It will be understood that both these figures are by way of example, and operator 22 may use other values for the conduction velocity and for the acceptable error.

Alternatively the conduction velocity may be calculated after steps 154 and 156 below have been implemented. In this case a wavefront, of a conduction wave originating from the arrythmia, is mapped from locations and LAT values of points found in step 156. The conduction velocity may be calculated from pairs of points that are selected to have respective line segments, joining the points, that are parallel to an assumed wavefront vector of the conduction wave.

In a data acquisition step 154, ECG signal data and positional signals are acquired from each of electrodes 50 of the probe.

In an analysis step 156, processor 40 uses the positional signals to first identify locations of points 80, and then construct a 3D triangular mesh of the surface of the heart chamber. The mesh is constructed by joining the points with edges, as described above with reference to FIG. 2, so forming a mesh with triangle vertices 80 and triangle sides 84. The mesh and/or the surface generated by the mesh may be presented to operator 22 on display 48.

The processor also analyzes the ECG signals to find the LAT values for each point 80 on the heart chamber surface contacted by electrodes 50, as described above with reference to FIG. 3.

In a pair selection step 160, a pair of locations on the surface of the heart chamber, i.e., two locations that the processor identifies in step 156, are selected. The locations are herein termed $X_1$, $X_2$. In the following description the selection is assumed to be performed by operator 22, typically using the map presented to the operator in step 156.

Once the pair has been selected, the processor determines the LAT values for each of the ECG signals of the pair, and then finds the difference in LAT values $\Delta t$. The processor then uses equation (1), with the conduction velocity v value set in step 150, to determine a path length difference, the LAT-derived distance, $\Delta P$, from the single source to the selected pair of locations.

In a plurality of locations generation step 164, the processor finds possible locations for the origin of the single-source arrythmia, herein assigned the label S, by finding locations of S that satisfy equation (4):

$$SX_1 - SX_2 = v \cdot \Delta t \qquad (4)$$

where $SX_2$ is the distance on the surface of the heart chamber between points S and $X_2$, and $SX_1$ is the distance on the surface of the heart chamber between points S and $X_1$.

The LAT-derived distance for points $X_1$, $X_2$ is the product $v \Delta t$.

(Equation (4) has the same form as equations (2) and (3); only the point identifiers have been changed.)

In order to check if equation (4) is satisfied, processor 40 calculates values of $SX_1$ and $SX_2$ separately, as follows:

For point $X_1$ the processor finds the shortest distances, along sides 84, to each of the vertices 80 acquired in step 156. The processor also finds the shortest distances, along sides 84, from $X_2$ to each of these vertices. In one embodiment the processor uses Dijkstra's algorithm to find the shortest distances.

For each of the vertices 80, the processor finds the difference $\Delta$ in the shortest distances.

In a comparison step 168, for each of the vertices 80, the processor checks if the difference $\Delta$ is close to the path length difference value $\Delta P$ found in step 160. I.e., the processor checks if the expression (5) is correct.

$$|\Delta - \Delta P| \leq E \qquad (5)$$

where E is the margin of error set in initial step 156.

If comparison 168 returns negative, the vertex 80 being checked is not considered to be a possible origin of the arrythmia. In this case control proceeds to a comparison step 172 where the processor checks if all the vertices have been checked for the locations selected in step 160*d*

If comparison step 168 returns positive, the vertex 80 being checked is a possible origin of the arrythmia. In this case processor 40 may mark the vertex on the map presented to the operator in a mark vertex step 176, and control continues to comparison step 172.

As stated above, in comparison step 172 the processor checks if all vertices have been checked for the locations selected in step 160. If the comparison returns negative, i.e., all vertices have not been checked, control returns to step 164.

If comparison step 172 returns positive, the processor continues to a further comparison step 180, wherein the processor checks if more than one pair of locations, chosen in step 160, has been selected and analyzed in the iteration of steps 164, 168, 176, and 172.

If multiple pairs of locations have not been selected (comparison 180 returning negative), i.e., only one pair of locations has been selected in step 160, then the processor selects another pair of locations, from those found in step 156, in a select pair location step 184. Control then returns to step 160, where the new location pair is analyzed.

Typically, locations of each pair are selected to be distinct, so that for two pairs there are four distinct locations. However, in some embodiments, any two pairs may have one common location, so that in these cases there are three distinct locations.

If comparison 180 returns positive, then two or more pairs of locations have been selected and analyzed. For each pair vertices have been marked, in step 176, as a locus of possible points for the arrythmia origin, and so there are two or more loci marked on the map. As described above, the intersection of the multiple loci corresponds to the predicted origin of the arrythmia, so that when comparison 180 returns positive, in a final step 188 of the flowchart, processor 40 may mark the loci intersection as the predicted arrythmia origin on the map.

In comparison step 180, the processor may stop the return to step 160 once a predetermined number of pairs of locations has been has been checked, and the number may be set by operator 22. In one embodiment the predetermined number of pairs is 10, from 20 locations. Alternatively, rather than the processor checking if multiple pairs have been checked, the operator may stop the return to step 160 once two or more location pairs have been checked, and invoke final step 188 so that the processor marks the intersection.

The description above has assumed that the processor measures distances, from each location selected in step 160, to triangle vertices along sides 184. The distances are measured so that the processor can find the shortest distance to a triangle vertex.

Figure 6:
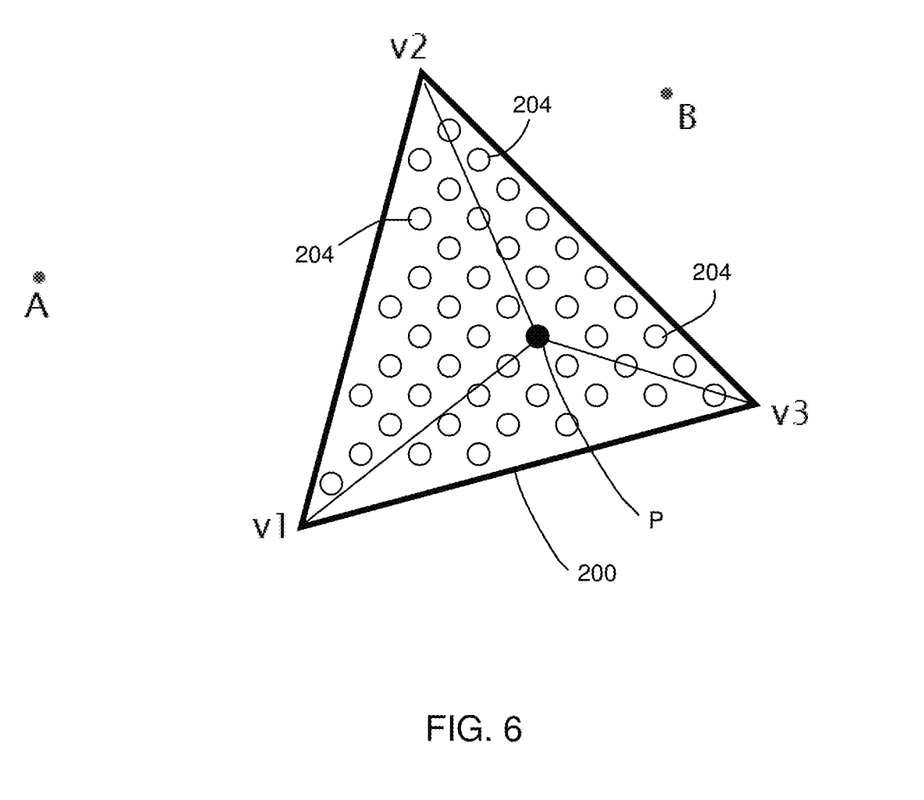
FIG. 6 illustrates a method for measuring distances to pairs of locations, according to an embodiment of the present invention.

FIG. 6 illustrates an alternative method for measuring distances to pairs of locations, according to an embodiment of the present invention. Rather than measuring to triangle vertices, the processor may measure distances from the selected locations, along edges 84, to a sample point P in a given triangle of the mesh generated in step 156. As described above with reference to FIG. 2, processor 40 typically covers triangles of the triangular mesh with equally spaced sample points. FIG. 6 illustrates a triangle 200 of the triangular mesh, and sample points 204 within the triangle. An example of the sample points has been assigned a label P. Thus, in FIG. 6, if point A is one of the selected pair of locations in step 160, the processor first calculates distances from A to vertices V1, V2, V3 of triangle 200, along edges 84 of triangles (not shown in the figure) connecting to triangle 200. The processor then sums the lengths V1P, V2P, and V3P to find possible distances from A to point P. The processor performs a similar calculation for point B as the other location of the selected pair.

The description of the flowchart of FIG. 5 may be adapted, mutatis mutandis, to use the alternative method for measuring distances to pairs of locations described with reference to FIG. 6, and thus find one or more sample points corresponding to a predicted origin of the arrythmia.

The inventors have tested an embodiment of the present invention using data from patients who have undergone successful ablation. The following summarizes the results of the test.

Figure 7:
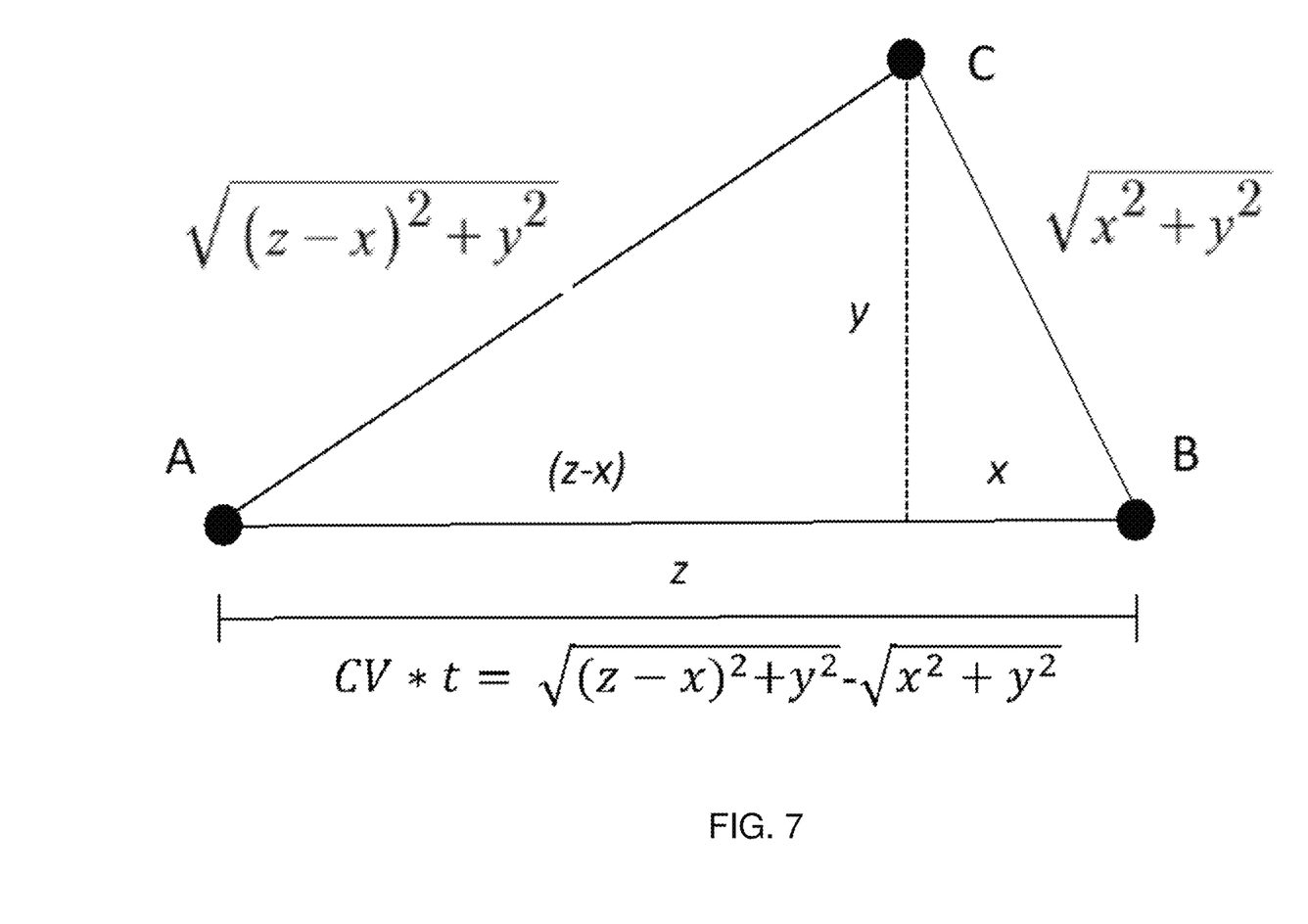
FIG. 7 is a schematic diagram illustrating, from a conceptual point of view, how an origin of an arrythmia may be determined, according to an embodiment of the present invention.

FIG. 7 is a schematic diagram illustrating, from a conceptual point of view, how an origin of an arrythmia may be determined, according to an embodiment of the present invention. The figure assumes that a selected pair of locations, such as locations A, B of FIG. 4, have been drawn on a plane surface, herein assumed to be an xy plane. The figure further assumes that points A, B are separated by a distance z, and that a point C in the plane is a possible origin of an arrythmia.

As for the system described above with reference to FIG. 4, there is a local activation time difference between locations A, B, in the figure assumed to be t. There is thus, again as for the system of FIG. 4, a path difference between CA and CB of CV·t, where CV is the conduction velocity of the wave from the arrythmia, giving the equation:

$$CV \cdot t = CA - CB \tag{6}$$

It will be appreciated that equation (6) corresponds to equations (2), (3), and (4) above.

As shown in the figure, if C is a vertical distance y above AB, and a horizontal distance x from B, then both CA and CB can be expressed in terms of x, y, and z. The expressions are presented in the figure, and substituting them into equation (6) gives $$CV \cdot t = \sqrt{(z-x)^2 + y^2} - \sqrt{x^2 + y^2} \tag{7}$$

Assuming CV, t and z are known, equation (7) can be solved for possible values of (x,y) for C, the values (x,y) generating a prediction curve of possible positions in the plane of the origin of the arrythmia.

If another pair of locations in the plane is selected, then the other pair generates a second prediction curve of possible positions of the origin of the arrythmia in the plane, and the intersection of the two lines corresponds to a predicted position for the origin of the arrythmia in the plane.

Figure 8:
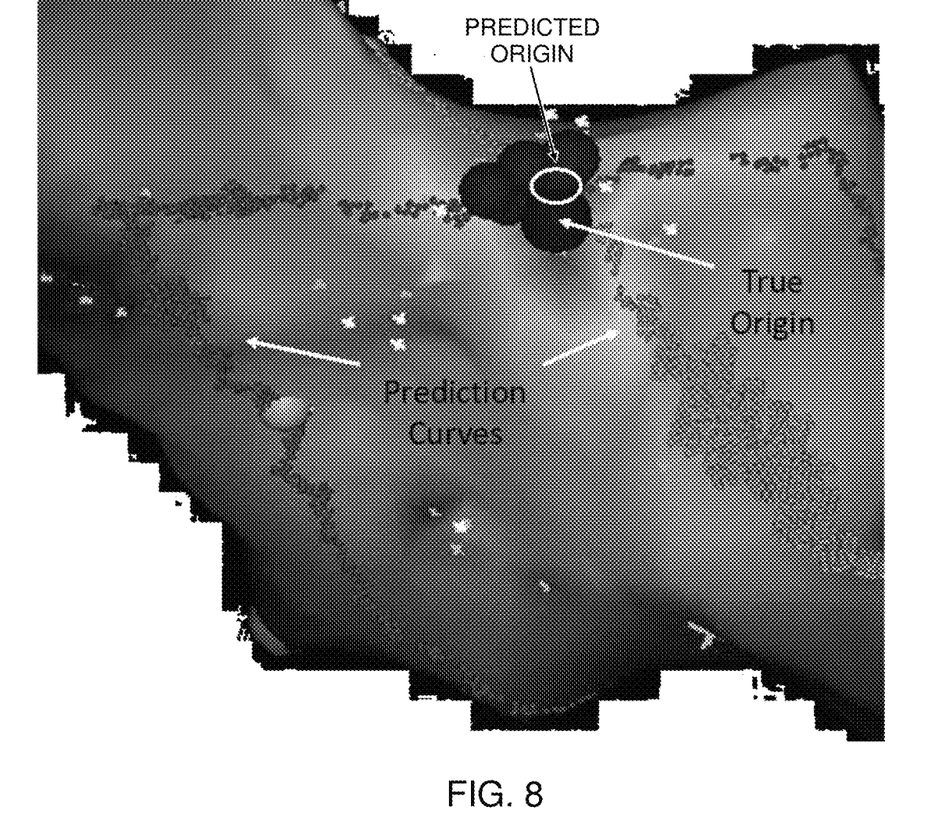
FIG. 8 is a schematic diagram illustrating a result obtained by the inventors, according to an embodiment of the present invention.

FIG. 8 is a schematic diagram illustrating a result obtained by the inventors, according to an embodiment of the present invention. Prediction curves for two pairs of locations were plotted on a 3D electroanatomic map where premature ventricular contraction (PVC) was occurring. One prediction curve comprises sets of dark gray points; a second prediction curve comprises sets of light gray points. (The actual map was in color, and the curves were in different colors.)

The intersection of the two curves is marked in the figure by a white ellipse, corresponding to the predicted origin of the arrythmia. The true origin, corresponding to a region where ablation was performed successfully, is shown in the figure, and is very close to the predicted origin.

Figure 9:
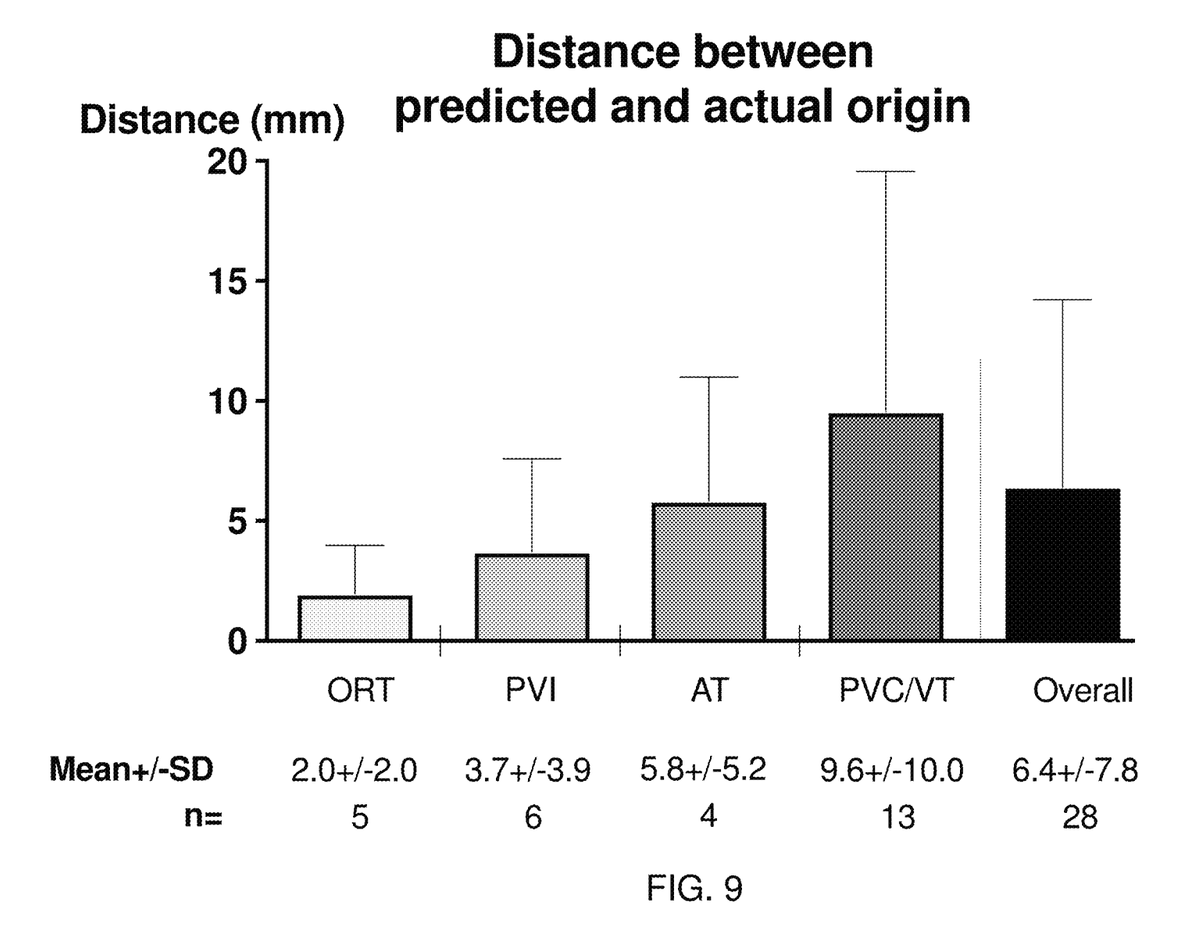
FIG. 9 is a diagram of results obtained by the inventors, according to an embodiment of the present invention.

FIG. 9 is a diagram of results obtained by the inventors, according to an embodiment of the present invention. Patients with successful ablation of a focal wavefront, as confirmed by traditional mapping and successful ablation with a focal ablation lesion, were retrospectively enrolled. Two or more pairs of prediction curves were generated in each patient. For each prediction curve conduction velocity was assessed in each patient using point pairs parallel to a mapped wavefront vector.

The main outcome was the distance between the predicted and the true origins for each prediction curve pair.

The inventors produced prediction curves for 28 cases. As shown in the figure, the overall results for the 28 intersections gave the distance between the predicted and true origins of the wavefront generated by the arrythmia as 6.4±7.8 mm. The figure also gives a breakdown of distances between predicted and true origins for different types of arrythmia.

In the figure "ORT" is orthodromic reciprocating tachycardia, "PVI" is pulmonary vein isolation, "AT" is atrial tachycardia, and "PVC/VT" is premature ventricular contraction/ventricular tachycardia.

Using univariate analysis, accuracy was found to be related to chamber of origin, conduction velocity, the standard deviation of conduction velocity measurements, the distance between the point pairs, and the cycle length of the rhythm, but not to the average distance of the point pairs to the wavefront origin or to the activation timing between the point pairs. Using multivariate analysis only chamber of origin was significant.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:

inserting a probe into a chamber of a heart of a human subject, the probe comprising at least two pairs of electrodes at a distal end thereof;

generating location signals indicative of location coordinates of the distal end of the probe;

acquiring from positions on a surface of the chamber respective electrical signals in response to a conduction wave traversing the surface;

processing the location signals to generate and present on a display a three-dimensional (3D) representation of the surface;

deriving respective local activation times (LATs) from the respective electrical signals at the positions on the surface;

calculating a first time difference between the respective LATs at a first pair of the positions on the surface and a second time difference between the respective LATs at a second pair of the positions on the surface;

calculating first and second LAT-derived distances as respective products of the first time difference and the second time difference with a conduction velocity of the conduction wave;

identifying an origin of an arrhythmia at a location on the surface such that a first difference in distances over the surface from the location to the first pair of the positions is equal to the first LAT-derived distance, and a second difference in distances over the surface from the location to the second pair of the positions is equal to the second LAT-derived distance;

marking the identified origin on the representation of the surface on the display;

generating a triangular mesh from the location coordinates, and wherein the distances over the surface comprise shortest distances measured along edges of the mesh;

covering the triangular mesh to form a smooth continuous 3D surface;

displaying a graphic representation of the smooth 3D surface on the display;

specifying equally spaced sample points on the triangular mesh; and using the sample points to perform discrete calculations on the continuous 3D surface.

2. The method according to claim 1, wherein the arryth­mia comprises a single source arrythmia.

3. The method according to claim 1, and comprising calculating the conduction velocity in response to a selected pair of points on the surface, the points being connected by a line segment parallel to a wavefront vector, and having respective LATs and positions.

4. The method according to claim 1, wherein the first difference in distances is equal to the first LAT-derived distance within a preset margin of error, and wherein the second difference in distances is equal to the second LAT-derived distance within the preset margin of error.

5. The method according to claim 4, wherein the preset margin of error is 1 mm.

* * * * *